(12) United States Patent
Nunome

(10) Patent No.: US 6,497,657 B2
(45) Date of Patent: Dec. 24, 2002

(54) REMOTE DIAGNOSIS SYSTEM

(75) Inventor: Tomohiro Nunome, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/778,799

(22) Filed: Feb. 8, 2001

(65) Prior Publication Data

US 2001/0037056 A1 Nov. 1, 2001

(30) Foreign Application Priority Data

May 1, 2000 (JP) ........................................ 2000-132344

(51) Int. Cl.⁷ ................................................. A61B 5/00
(52) U.S. Cl. .................... 600/300; 128/904; 128/923
(58) Field of Search ................................. 600/300, 301, 600/485, 490, 494, 549; 128/903, 904, 923

(56) References Cited

U.S. PATENT DOCUMENTS 5,462,051 A * 10/1995 Oka et al. .................... 600/300
5,868,669 A * 2/1999 Iliff ............................. 600/300
5,911,687 A * 6/1999 Sato et al. .................... 600/300

FOREIGN PATENT DOCUMENTS

JP          A 10-143573          5/1998

* cited by examiner

*Primary Examiner*—Eric F. Winakur
*Assistant Examiner*—David McCrosky
(74) *Attorney, Agent, or Firm*—Oliff & Berridge, PLC

(57) ABSTRACT

A remote diagnosis system including a patient-side device including a physical-information obtaining device which obtains a piece of current physical information from a patient, a plurality of doctor-side devices which are provided in a plurality of medical institutions, respectively, that are remote from the patient-side device and each of which can receive the piece of current physical information of the patient from the patient-side device, a preliminary-diagnosis device for making, based on the piece of current physical information obtained by the physical-information obtaining device, a preliminary diagnosis about whether the patient needs a proper diagnosis to be made by a doctor, and a physical-information transmitting device for transmitting, when the preliminary-diagnosis device makes a preliminary diagnosis that the patient needs a proper diagnosis to be made by a doctor, the piece of current physical information to at least one selected doctor-side device out of the plurality of doctor-side devices.

20 Claims, 4 Drawing Sheets

REMOTE DIAGNOSIS SYSTEM

BACKGROUND OF THE INVENTION

1. Field of the Invention

The present invention relates to a remote diagnosis system which transmits, to a medical institution, physical information obtained from a patient at a location (e.g., patient's home) remote from the medical institution, so that a doctor at the medical institution makes, based on the transmitted physical information, a medical diagnosis on the patient.

2. Related Art Statement

Japanese Patent Document No. 10-143573 discloses a remote diagnosis system which includes a physical-information obtaining device that is placed in a house of a patient and obtains physical information (e.g., blood pressure, heart rate, etc.) from the patient and which transmits the obtained physical information to a doctor-side terminal device that is placed in a medical institution (e.g., hospital, doctor's office, etc.) remote from the patient's house. The prior remote diagnosis system additionally includes a preliminary-diagnosis device which automatically makes a preliminary diagnosis about the physical information, before the physical information is transmitted to the medical institution.

More specifically described, the preliminary-diagnosis device makes a preliminary diagnosis by judging whether the physical information obtained from the patient is greater than a threshold value, and selects, from a plurality of doctor-side terminal devices assigned to a plurality of doctors, one doctor-side terminal device assigned to one doctor who is suitable for making a proper diagnosis based on the physical information and the preliminary diagnosis, so that the remote diagnosis system transmits the physical information to the selected doctor-side terminal device. Thus, the preliminary diagnosis is utilized to transmit the physical information to the suitable doctor who can make a correct diagnosis on the patient. In addition, when the preliminary diagnosis indicates that the physical information is obviously normal and the patient does not need a proper diagnosis by a doctor, the remote diagnosis system does not transmit the physical information to any doctor-side terminal devices. Thus, a total amount of physical information transmitted to each doctor is decreased, and each doctor can more quickly make a proper diagnosis about the thus decreased amount of physical information only.

Thus, in the case where the preliminary-diagnosis device makes respective "abnormality" preliminary diagnoses about different sorts of physical information, the prior remote diagnosis system transmits the different sorts of physical information to different doctor-side terminal devices assigned to different doctors who are suitable for diagnosing the different sorts of physical information, respectively. However, in the case where the preliminary-diagnosis device makes respective "abnormality" preliminary diagnoses about different pieces of physical information of one sort, the prior remote diagnosis system transmits all the different pieces of physical information to one and same doctor-side terminal device assigned to one and same doctor who is suitable for diagnosing the one sort of physical information. This largely limits the degree of freedom of choice of the patient who could freely go and see any one of a plurality of doctors at a plurality of medical institutions. In addition, since only one doctor makes a final diagnosis about each piece of physical information, the final diagnosis may not be sufficiently accurate or reliable.

SUMMARY OF THE INVENTION

It is a first object of the present invention to provide a remote diagnosis system which includes a plurality of doctor-side devices any one of which can be selected by a patient.

It is a second object of the present invention to provide a remote diagnosis system which includes a plurality of doctor-side devices which can provide a patient with accurate or reliable diagnoses.

Each of the above objects has been achieved by the present invention. According to a first feature of the present invention, there is provided a remote diagnosis system comprising at least one patient-side device including at least one physical-information obtaining device which obtains at least one piece of current physical information from at least one patient; a plurality of doctor-side devices which are provided in a plurality of medical institutions, respectively, that are remote from the patient-side device and each of which can receive the piece of current physical information of the patient from the patient-side device; a preliminary-diagnosis means for making, based on the piece of current physical information obtained by the physical-information obtaining device, a preliminary diagnosis about whether the patient needs a proper diagnosis to be made by a doctor; and a physical-information transmitting means for transmitting, when the preliminary-diagnosis means makes a preliminary diagnosis that the patient needs a proper diagnosis to be made by a doctor, the piece of current physical information to at least one doctor-side device of the plurality of doctor-side devices that has been selected by the patient.

In the present remote diagnosis system, when the preliminary-diagnosis means makes a preliminary diagnosis that the patient needs a proper diagnosis to be made by a doctor, the physical-information transmitting means transmits the piece of current physical information obtained by the physical-information obtaining device, to one or more doctor-side devices of the plurality of doctor-side devices that have been selected by the patient. Thus, as in the case where the patient actually goes and sees one or more doctors at one or more medical institutions out of a number of medical institutions, the physical information obtained from the patient is transmitted to one or more doctor-side devices selected by the patient out of the plurality of doctor-side devices, so that the physical information or the patient is diagnosed by one doctor before the one doctor-side device, or each of two or more doctors before the two or more doctor-side devices.

According to a second feature of the present invention, there is provided a remote diagnosis system comprising at least one patient-side device including at least one physical-information obtaining device which obtains at least one piece of current physical information from at least one patient; a plurality of doctor-side devices which are provided in a plurality of medical institutions, respectively, that are remote from the patient-side device and each of which can receive the piece of current physical information of the patient from the patient-side device; a preliminary-diagnosis means for making, based on the piece of current physical information obtained by the physical-information obtaining device, a preliminary diagnosis about whether the patient needs a proper diagnosis to be made by a doctor; and a physical-information transmitting means for transmitting, when the preliminary-diagnosis means makes a preliminary diagnosis that the patient needs a proper diagnosis to be made by a doctor, the piece of current physical information to each of the plurality of doctor-side devices.

In the present remote diagnosis system, when the preliminary-diagnosis means makes a preliminary diagnosis that the patient needs a proper diagnosis to be made by a doctor, the physical-information transmitting means transmits the piece of current physical information obtained by the physical-information obtaining device, to each of of the plurality of doctor-side devices. Since the physical information obtained from the patient is transmitted to the plurality of doctor-side devices provided at the plurality of medical institutions, the physical information or the patient can be accurately or reliably diagnosed by two or more doctors before the two or more doctor-side devices.

According to a third feature of the present invention, the preliminary-diagnosis means comprises means for judging whether the piece of current physical information falls within a first reference range, and means for making, when it is judged that the piece of current physical information does not fall within the first reference range, a preliminary diagnosis that the patient needs a proper diagnosis to be made by a doctor, and each of the doctor-side devices comprises a reference-range changing means for transmitting, to the preliminary-diagnosis means, a second reference range and changing the first reference range to the second reference range, so that the preliminary-diagnosis means judges whether the piece of current physical information falls within the second reference range.

In the present remote diagnosis system, a doctor before each doctors-side device can operate the reference-range changing means to change the current reference range to a more appropriate reference range, so that the preliminary-diagnosis means judges whether each piece of physical information falls within the more appropriate reference range. Therefore, the preliminary-diagnosis means can make a more accurate preliminary diagnosis. This leads to reducing the overall load exerted to each doctor and promoting each doctor to make more quickly a proper diagnosis on only the physical information judged as being abnormal by the preliminary-diagnosis means.

According to a fourth feature of the present invention, the preliminary-diagnosis means comprises means for judging whether the piece of current physical information falls within a first reference range proper for the patient; means for making, when it is judged that the piece of current physical information does not fall within the first reference range, a preliminary diagnosis that the patient needs a proper diagnosis to be made by a doctor; and a memory device which stores a plurality of first reference ranges respectively proper for a plurality of patients including the patient.

In the present remote diagnosis system, the preliminary-diagnosis means can make a more accurate preliminary diagnosis. This leads to reducing the overall load exerted to each doctor and promoting each doctor to make more quickly a proper diagnosis on only the physical information judged as being abnormal by the preliminary-diagnosis means.

According to a fifth feature of the present invention, each of the doctor-side devices comprises a reference-range changing means for transmitting, to the preliminary-diagnosis means, a second reference range proper for the patient and changing the first reference range proper for the patient to the second reference range proper for the patient, so that the preliminary-diagnosis means judges whether the piece of current physical information falls within the second reference range proper for the patient.

In the present remote diagnosis system, a doctor before each doctors-side device can operate the reference-range changing means to change the current reference range proper for each patient to a more appropriate reference range proper for each patient, so that the preliminary-diagnosis means judges whether each piece of physical information falls within the more appropriate reference range proper for each patient. Therefore, the preliminary-diagnosis means can make a more accurate preliminary diagnosis.

According to a sixth feature of the present invention, the patient-side device comprises a display device; and a display control means for controlling the display device to display the preliminary diagnosis made by the preliminary-diagnosis means.

The present remote diagnosis system enables the patient to from, from the preliminary diagnosis displayed on the display device, whether he or she should go and see a doctor to obtain a doctor's proper diagnosis about his or her physical information.

According to a seventh feature of the present invention, the remote diagnosis system comprises a plurality of patient-side devices each of which includes at least one physical-information obtaining device which obtains at least one piece of current physical information from a corresponding one of a plurality of patients including the patient, the preliminary-diagnosis means comprises a memory device which stores, for each of the plurality of patients, at least one piece of past physical information which had been obtained by the physical-information obtaining device of a corresponding one of the plurality of patient-side devices, and the physical-information transmitting means transmits, to the doctor-side device, the piece of current physical information with the piece of past physical information stored for the patient in the memory device.

The present remote diagnosis system enables a doctor to make a proper diagnosis about the patient based on not only the piece of current physical information but also one or more pieces of past physical information. Therefore, the doctor can make a more accurate diagnosis on the patient.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Hereinafter, there will be described a remote diagnosis system 10 embodying the present invention, by reference to the accompanying drawings.

Figure 1:
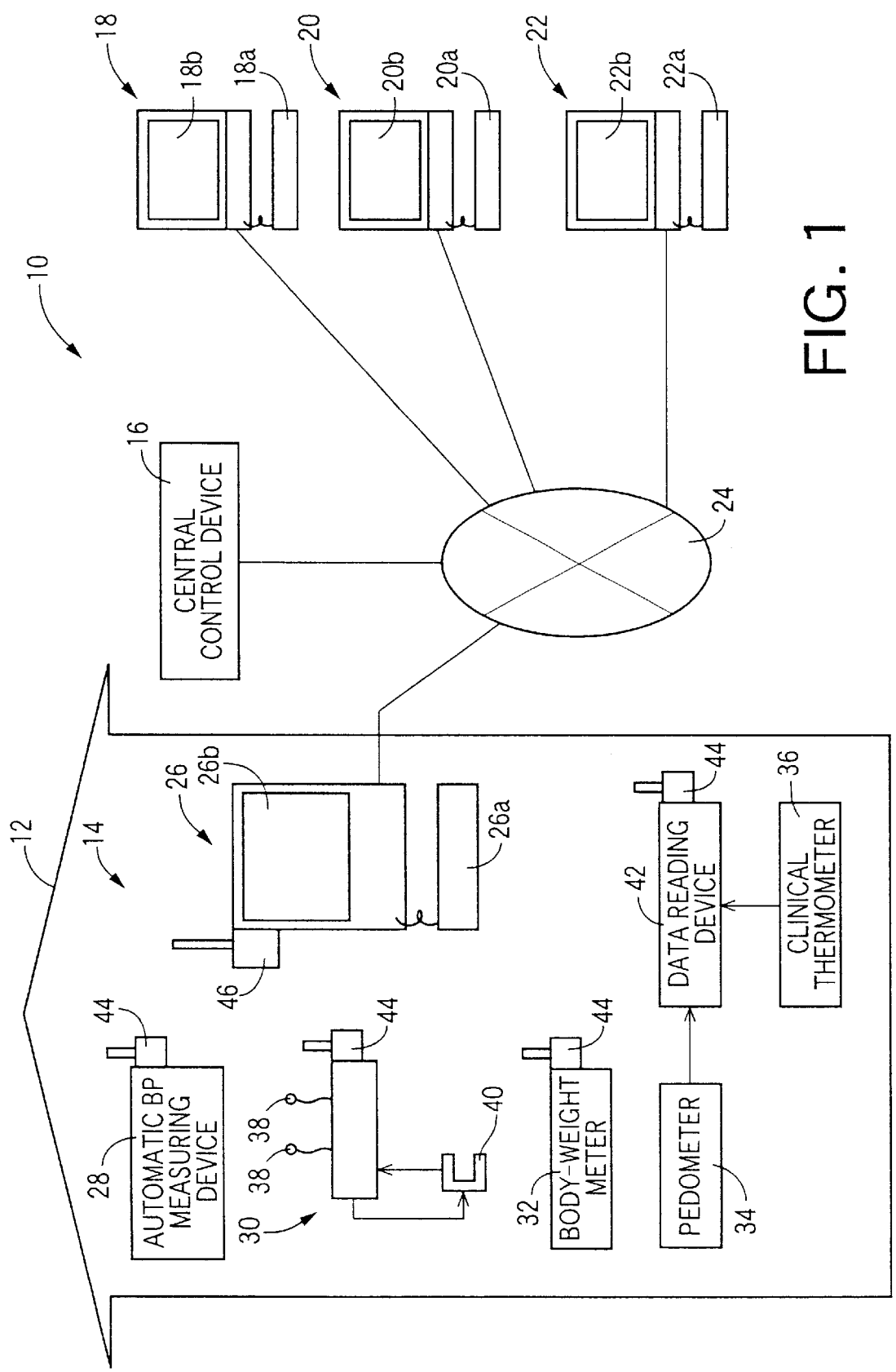
FIG. 1 is a diagrammatic view for explaining a general construction of a remote diagnosis system embodying the present invention.

In FIG. 1, the remote diagnosis system 10 includes a patient-side device 14 which is provided or placed in a house 12 of a patient; a central control device 16; a plurality of (three in FIG. 3) doctor-side terminal devices 18, 20, 22 which are provided or placed in a plurality of (three) medical institutions, respectively; and a communication network 24 which connects the devices 14, 16, 18, 20, 22 to one another.

The patient-side device 14 includes at least one physical-information obtaining device which obtains, from the patient, at least one sort of physical information which is useful for making a diagnosis on a physical condition of the patient; and a single patient-side terminal device 26. In the embodiment shown in FIG. 1, the patient-side device 14 includes, as the physical-information obtaining devices, an automatic blood-pressure (BP) measuring device 28, a pulse-wave-propagation-velocity-relating-information obtaining device 30, a body-weight meter 32, a pedometer 34, and a clinical thermometer 36.

The automatic BP measuring device 28 includes an inflatable cuff (not shown), and measures one or more blood-pressure values BP and a heart rate HR of the patient based on a pressure-pulse-wave signal which is detected from the cuff while a pressing force (i.e., air pressure) of the cuff being wound around a body portion (e.g., upper arm) of the patient is gradually changed.

The pulse wave propagation velocity (PWV) relating information obtaining device 30 obtains information relating to a velocity PWV at which a pulse wave propagates between two body portions of the patient. The PWV-relating information may be a velocity PWV itself, or a pulse-wave propagation time DT in which the pulse wave propagates between the two body portions of the patient. In the present embodiment, the PWV-relating-information obtaining device 30 includes a plurality of electrodes 38 which are adapted to be set on respective predetermined body portions of the patient to detect an electrocardiograph (ECG; action potential of the heart muscle) as a pulse wave which is produced in synchronism with heartbeat of the patient. The obtaining device 30 additionally includes a photoelectric-pulse-wave sensor 40 which is worn on a finger of the patient to detect a photoelectric (or volumetric) pulse wave representing the change of volume of blood present in capillaries of the finger. The obtaining device 30 calculates, as the pulse-wave propagation time DT, a time difference between the time of detection of a periodic point on the waveform of the ECG detected through the electrodes 38 and the time of detection of a corresponding periodic point on the waveform of the photoelectric pulse wave detected by the pulse-wave sensor 40. In addition, the obtaining device 30 calculates the pulse-wave propagation velocity PWV by dividing the propagation time DT by a standard distance (i.e., constant value) between the heart and the finger.

The body-weight meter 32 measures a body weight of the patient, the pedometer 34 counts a number $N_W$ of steps of the patient, and the clinical thermometer 36 measures a body temperature T of the patient. A data reading device 42 is connected to the pedometer 34 and the thermometer 36, and reads the step number $N_W$ counted by the pedometer 34 and the body temperature T measured by the thermometer 36. Each of the BP measuring device 28, the PWV-relating-information obtaining device 30, the body-weight meter 32, and the data reading device 42 additionally includes a signal transmitter 44 which transmits a corresponding sort of physical information to a signal receiver 46 of the patient-side device 26.

The patient-side terminal device 26 additionally includes an input device 26a, a display device 26b, and a computer (not shown), and receives, via the signal receiver 46, the various sorts of physical information from the respective signal transmitters 44 of the physical-information obtaining devices 28, 30, 32, 34, 36. The terminal device 26 transmits the received information to the central control device 16 via the communication network 24. The input device 26a includes a special portion which is operable for inputting an identification data or signal SI (e.g., identification (ID) number, finger print, voice print, etc.) identifying the patient. In addition, the input device 26a includes an input key which is operable for selecting one or more of the plurality of doctor-side terminal devices 18, 20, 22. The display device 26b includes a cathode ray tube (CRT) or a liquid crystal display (LCD). A television set may be used as the display device 26b.

So long as the central control device 16 is connected to the doctor-side terminals 18, 20, 22 via the communication network 24, the control device 16 may be provided anywhere. For example, the control device 16 may be provided in one of the respective medical institutions in which the doctor-side terminals 18, 20, 22 are provided, or in a medical institution different from the above medical institutions. The central control device 16 includes a computer, and is connected via the communication network 24 to a plurality of patient-side devices 26 (only one device 26 is shown in FIG. 1) which are provided in respective houses of a plurality of patients. The control device 16 additionally includes a memory device 16a (FIG. 3) which stores, for each of the patients, the various sorts of physical information supplied from a corresponding one of the patient-side devices 26, such that the sorts of physical information is associated with the identification data SI identifying the each patient. The memory device 16a may be provided by a random access memory (RAM), a magnetic disc device (HDD), or a photo-magnetic disc device (MO).

Each of the doctor-side terminal devices 18, 20, 22 is provided at a place where the each device 18, 20, 22 is operable by one or more doctors who can diagnose, as specialists, respective sorts of physical information. The terminal devices 18, 20, 22 include respective computers, respective keyboards 18a, 20a, 22a each as an input device, and respective display devices 18b, 20b, 22b.

The communication network 24 may be provided by a public-telephone-line network, a wire or wireless LAN (local area network), a satellite communication line, or a cable-television-line network.

Figure 2:
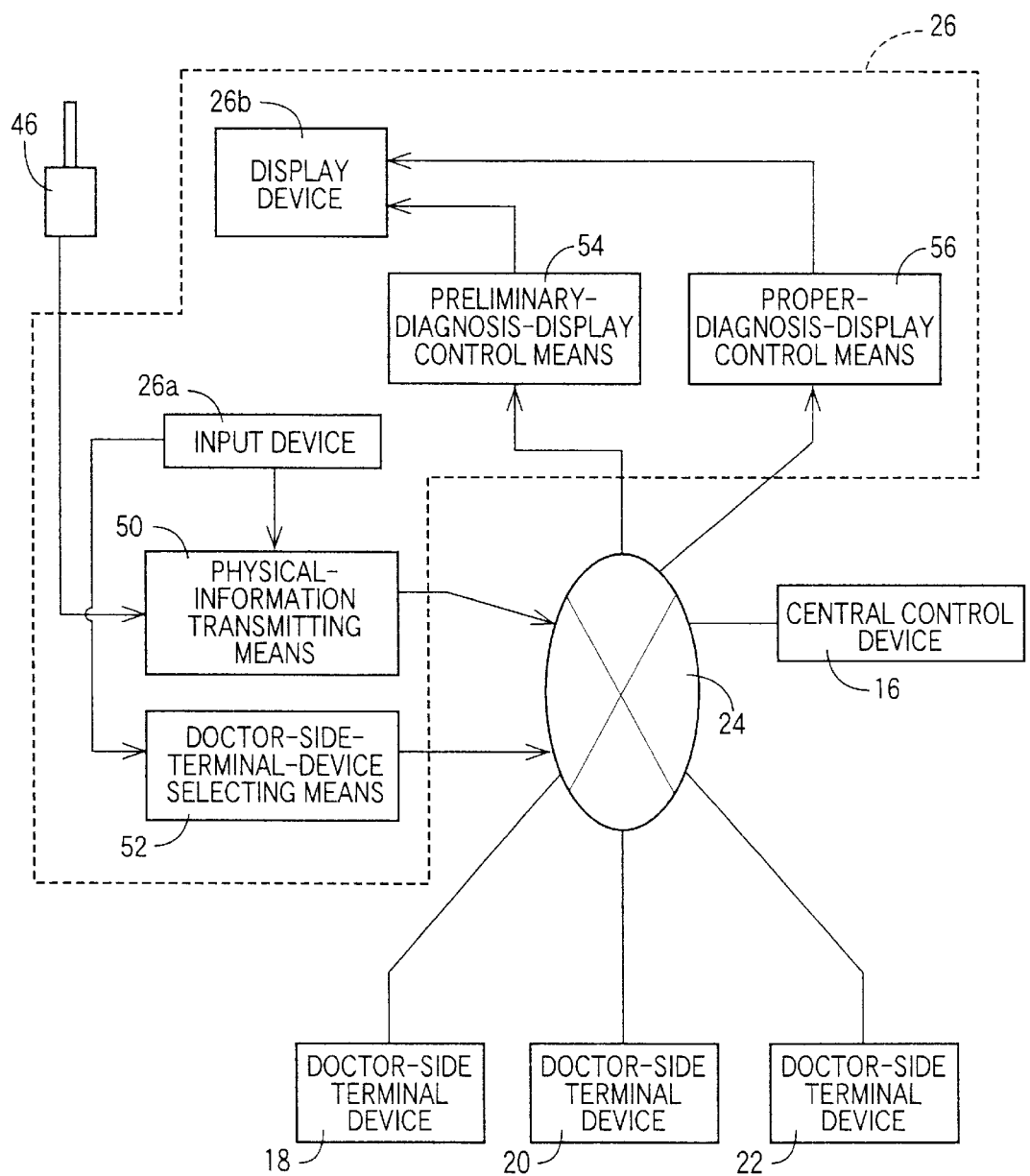
FIG. 2 is a block diagram for explaining essential functions of a computer of a patient-side terminal device of the diagnosis system of FIG. 1.

FIG. 2 is a diagrammatic view for explaining essential functions of the computer of the patient-side terminal device 26. A physical-information transmitting means 50 transmits the various sorts of physical information (e.g., blood-pressure values BP, etc) received by the signal receiver 46, together with the identification data SI input through the input device 26a by the patient and identifying the patient, to the central control device 16 via the communication network 24. The time when the physical-information transmitting means 50 transmits the physical information may be a time when the signal receiver 46 receives each sort of physical information, or a time when a transmission-command signal is input through the input device 26a by the patient. In the first case, the each sort of physical information is transmitted with the patient-identification data SI that were input and registered in advance, to the central control device 16.

A doctor-side-terminal-device selecting means 52 produces, according to the patient's operation of the input device 26a for each sort of physical information, a designation signal SA to designate one or more doctor-side terminal devices which is or are selected from the plurality of doctor-side terminal devices 18, 20, 22 by the patient for the each sort of physical inforamtion, and transmits the designation signal SA to the central control device 16 via the communication network 24. Thus, the patient can select, for each sort of physical information, the doctor-side terminal device placed in one of the medical institutions to which his or her familiar doctor belongs, so that the familiar doctor may make a proper diagnosis about the each sort of physical information.

A preliminary-diagnosis display control means 54 operates the display device 26b to display a preliminary diagnosis which is transmitted from the central control device 16. A proper-diagnosis display control means 56 operates the display device 26b to display one or more proper diagnoses which is or are transmitted from one or more selected doctor-side terminal devices 18, 20, 22.

Figure 3:
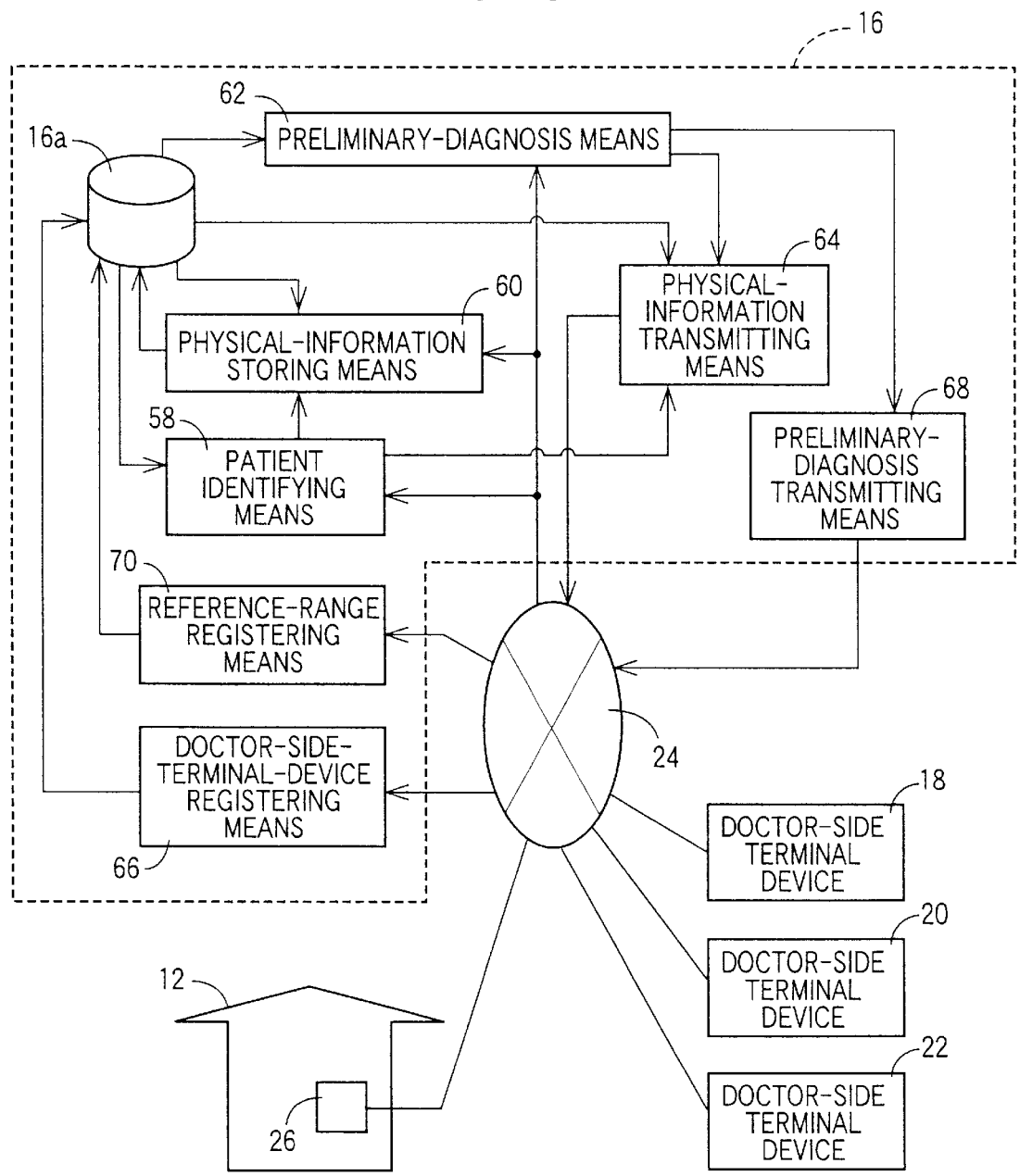
FIG. 3 is a block diagram for explaining essential functions of a computer of a central control device of the diagnosis system of FIG. 1.

FIG. 3 is a diagrammatic view for explaining essential functions of the computer of the central control device 16. A patient identifying means 58 compares the patient-identification signal SI transmitted from the patient-side terminal device 26 with each of a plurality of patient-identification signals SI which are stored in advance in the memory device 16a, and thereby identifies the patient or the patient-side device 26 who or which has transmitted the physical information with the signal SI to the central control device 16.

A physical-information storing means 60 identifies a sort of the physical information transmitted from the patient-side terminal device 26, based on physical-information-identification information added to the head or end of the physical information, and stores the physical information in an area of the memory device 16 that corresponds to the identified patient and the identified information sort.

A preliminary-diagnosis means 62 automatically judges whether the physical information transmitted from the patient-side terminal device 26 falls within a reference range proper for the identified information sort and, if a negative judgment is made, makes a preliminary diagnosis that the physical information needs a proper diagnosis to be made by a doctor. The reference range proper for each sort of physical information may be one which is proper for the identified patient, or one which can be widely used for many people. The reference range may have either one or both of an upper and a lower limit.

A physical-information transmitting means 64 transmits, if the preliminary-diagnosis means 62 makes a preliminary diagnosis that the current physical information transmitted from the patient-side terminal device 26 needs a proper diagnosis to be made by a doctor, the current physical information together with the patient's name and at least one piece of past physical information of the same sort stored in the memory device 16a, to one or more doctor-side terminal devices 18, 20, 22 which is or are registered in advance, for the sort of physical information, by a doctor-side-terminal-device registering means 66, described below. However, the transmitting means 64 may additionally transmit the other sorts of past physical information than the same sort of past physical information as the sort of the current physical information, to the registered doctor-side terminal device or devices 18, 20, 22.

A doctor-side-terminal-device registering means 66 registers, according to the designation signal SA transmitted from the patient-side terminal device 26, one or more doctor-side terminal devices 18, 20, 22 to which each sort of physical information transmitted from the patient-side terminal device 26 is to be transmitted by the physical-information transmitting means 64. The doctor-side terminal device or devices 18, 20, 22 is or are registered in the memory device 16a. When the registering means 66 receives another designation signal SA after having received one designation signal SA, the registering means 66 registers, in place of the one or more doctor-side terminal devices 18, 20, 22 registered according to the first signal SA, one or more doctor-side terminal devices 18, 20, 22 according to the second signal SA.

A preliminary-diagnosis transmitting means 68 transmits the preliminary diagnosis made by the preliminary-diagnosis means 62, via the communication network 24, to the patient-side terminal device 26 which transmitted the physical information on which the preliminary diagnosis was made.

A reference-range registering means 70 registers, in the memory device 16a, a reference range proper for each patient and each sort of physical information, that is transmitted from each of the doctor-side terminal devices 18, 20, 22, so that the reference range is used by the preliminary-diagnosis means 62 in judging whether the each sort of physical information obtained from the each patient falls within the reference range and making a preliminary diagnosis about whether the physical information needs a proper diagnosis to be made by a doctor.

Figure 4:
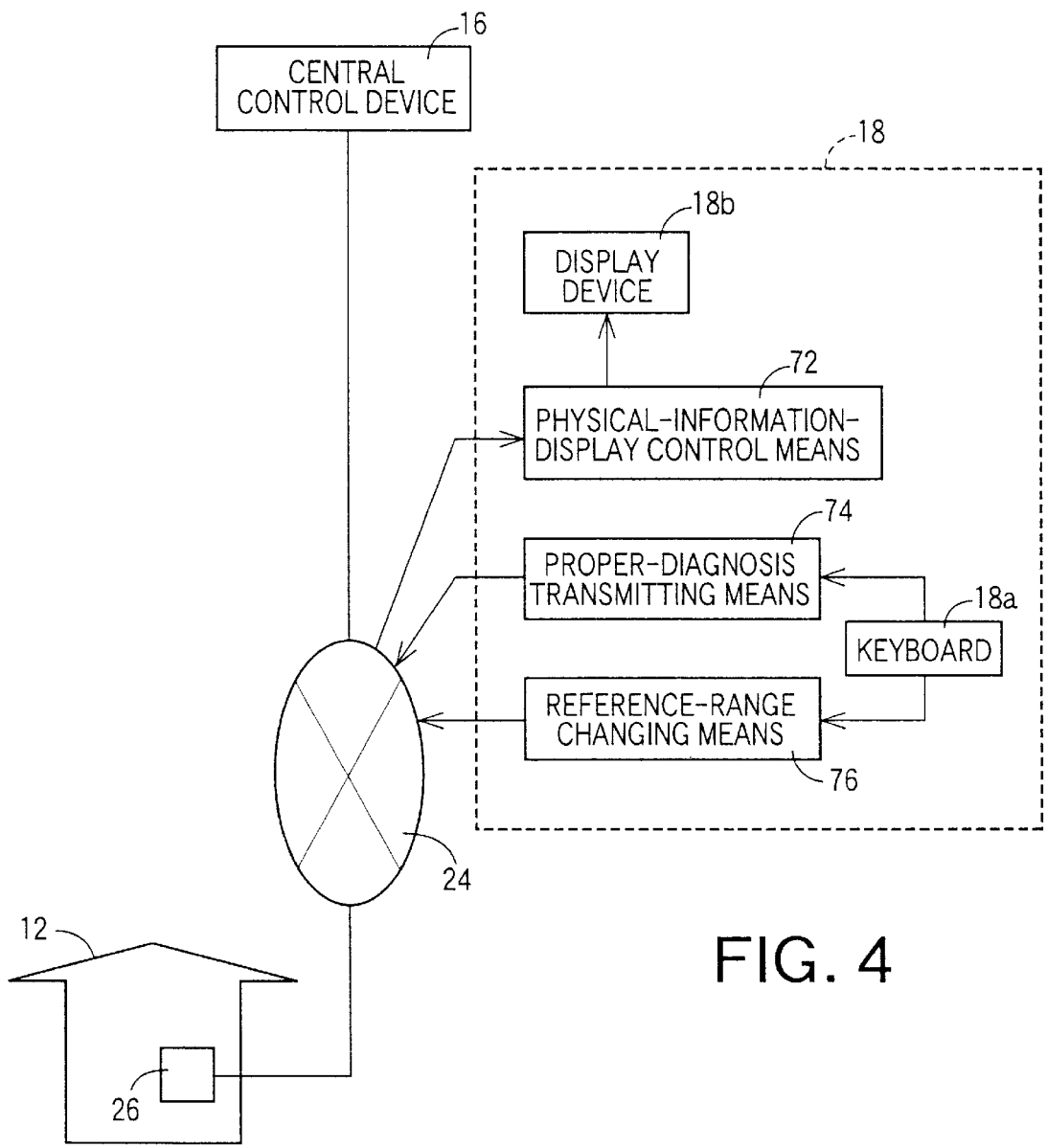
FIG. 4 is a block diagram for explaining essential functions of a computer of each of a plurality of doctor-side terminal devices of the diagnosis system of FIG. 1.

FIG. 4 is a diagrammatic view for explaining essential functions of the computer of the doctor-side terminal devices 18 that are the same as those of each of the doctor-side terminal devices 20, 22.

A physical-information-display control means 72 operates the display device 18b to display all the information transmitted from the central control device 16, that is, the physical information judged as being not normal by the preliminary-diagnosis means 62, the patient's name from which the physical information was obtained, and the one or more pieces of past physical information stored for the patient in the memory device 16a. A doctor who is familiar with the patient makes a proper or final medical diagnosis based on the information displayed on the display device 18b, and inputs the proper diagnosis and one or more medical advices to the patient, through the keyboard 18a.

A proper-diagnosis transmitting means 74 transmits the proper diagnosis made by the doctor and input through the keyboard 18a, and the medical advices, if any, to the patient-side terminal device 26 via the communication network 26.

A reference-range changing means 76 transmits, to the central control device 16 via the communication network 24, a new reference range which is input through the input device 18a by the doctor who judged that the current reference range which is used by the preliminary-diagnosis means 62 in making a preliminary diagnosis should be changed to the new reference range. In a first case where the current reference range is proper for each patient, the new reference range should also be proper for the each patient; and in a second case where the current reference range is widely usable for many people, the new reference range should also be widely usable for many people. The first case may be such that a reference range proper for a certain patient needs to be changed since it has been found that the patient has a chronic disease; and the second case may be such that a reference range usable for many people needs to be changed since an academic society has recently announced a more appropriate reference range.

It emerges from the foregoing description that when the preliminary-diagnosis means 62 makes a preliminary diagnosis that the physical information obtained by the physical-information obtaining device 28–36 needs to be properly diagnosed by a doctor, the physical-information transmitting means 64 transmits the physical information to one or more doctor-side terminal devices which was or were selected in advance by the patient from the plurality of doctor-side terminal devices 18, 20, 22. Thus, the physical information can be diagnosed by one or more doctors at one or more medical institutions selected by the patient, like in the case where the patient actually goes and sees the one or more doctors at the one or more medical institutions.

In addition, in the case where two or more doctor-side terminal devices were selected in advance by the patient from the plurality of doctor-side terminal devices 18, 20, 22, if the preliminary-diagnosis means 62 makes a preliminary diagnosis that the physical information needs to be properly diagnosed by a doctor, the physical-information transmitting means 64 transmits the physical information to the two or more selected doctor-side terminal devices. Thus, the physical information is diagnosed by two or more doctors at two or more medical institutions selected by the patient. Therefore, the patient can obtain a more accurate or reliable diagnosis.

Moreover, the reference-range changing means 76 and the reference-range registering means 70 cooperate with each other to enable a doctor to change the current reference range proper for each patient or widely usable for many people, to a new, more appropriate reference range, so that the new reference range is used by the preliminary-diagnosis means 62 in making a preliminary diagnosis. Therefore, the preliminary-diagnosis means 62 can make a more accurate preliminary diagnosis, and the overall burden to each doctor can be reduced. This enables each doctor to make more quickly a proper or final diagnosis.

In addition, in the case where the reference range for each sort of physical information is one which is proper for each patient, the preliminary-diagnosis means 62 can make a more accurate preliminary diagnosis. Therefore, the overall burden to each doctor is reduced, and each doctor can more quickly make a truly needed diagnosis.

In addition, the preliminary-diagnosis-display control means 54 operates the display device 26b to display the preliminary diagnosis made by the preliminary-diagnosis means 62. Thus, the patient can know, from the preliminary diagnosis displayed on the display device, whether the physical information obtained from him or her should be properly diagnosed by a doctor.

Furthermore, the physical-information transmitting means 64 of the central control device 16 transmits the current physical information which is obtained from the patient and on which a preliminary diagnosis is made by the preliminary-diagnosis means 62, with one or more pieces of past physical information stored in the memory device 16a for the patient, to the one or more selected doctor-side terminal devices 18, 20, 22.

Thus, one or more doctors before the one or more devices 18, 20, 22 can more accurately make a final diagnosis based on not only the current physical information but also the one or more pieces of past physical information.

While the present invention has been described in its preferred embodiment by reference to the drawings, it is to be understood that the invention may otherwise be embodied.

For example, the illustrated remote diagnosis system 10 includes the central control device 16 including the preliminary-diagnosis means 62 and the physical-information transmitting means 64, and accordingly the physical information obtained by the physical-information obtaining device 28–36 is transmitted to the central control device 16, so that the physical information is subjected to preliminary diagnosis by the control device 16 and, if being judged as being not normal, is transmitted from the control device 16 to one or more selected doctor-side terminal devices 18–22. However, the patient-side device 14 may additionally employ the preliminary-diagnosis means 62. In the latter case, the physical-information transmitting means 50 of the patient-side terminal device 26 may directly transmit the physical information to one or more selected doctor-side terminal devices 18–22, if the physical information is judged as being not normal by the preliminary-diagnosis means 62.

In the illustrated embodiment, the patient-side device 14 is provided in a patient's house 12. However, the device 14 may be provided in a company's office or a public office.

In the illustrated embodiment, the physical-information transmitting means 64 transmits not only the current physical information obtained from the patient and subjected to the preliminary diagnosis by the preliminary-diagnosis means 62, but also one or more pieces of past physical information stored for the patient in the memory device 16a, to one or more selected doctor-side terminal devices 18, 20, 22. However, the transmit transmitting means 64 may be modified to transmit the current physical information only.

In the illustrated embodiment, the patient-side device 14 includes the doctor-side-terminal-device selecting means 52, and the central control device 16 includes the doctor-side-terminal-device registering means 66, so that the patient himself or herself can select one or more doctor-side terminal devices 18, 20, 22 to which the physical information obtained from the patient is to be transmitted by the physical-information transmitting means 64. However, the physical-information transmitting means 64 may be modified to automatically select, based on the specific sort of the physical information judged as being not normal by the preliminary-diagnosis means 62, two or more appropriate doctor-side terminal devices from the plurality of doctor-side terminal devices 18–22, and transmit the physical information to each of the thus selected doctor-side terminal devices.

In the illustrated embodiment, the patient-side device 14 employs, as the physical-information obtaining devices, the automatic BP measuring device 28, the PWV-relating-information obtaining device 30, the body-weight meter or scale 32, the pedometer 34, and the clinical thermometer 36. However, the patient-side device 14 may employ, in addition to, or in place of, the above-indicated physical-information obtaining devices, an electrocardiograph (ECG) which obtains an electrocardiogram (ECG) from the patient and/or a phonocardiograph which detects one or more heart sounds from the patient.

It is to be understood that the present invention may be embodied with other changes, improvements and modifications that may occur to one skilled in the art without departing from the spirit and scope of the invention.

What is claimed is:

1. A remote diagnosis system comprising:
   at least one patient-side device including at least one physical-information measuring device which measures at least one current physical information value from at least one patient;
   a plurality of doctor-side devices which are provided in a plurality of medical institutions, respectively, that are remote from the patient-side device and each of which can receive the measured current physical information value of the patient from the patient-side device, wherein the at least one patient-side device further includes a doctor-side device selecting device operable by a patient to select at least one of the plurality of doctor-side devices;

a preliminary-diagnosis means for making, based on the physical information value measured by the physical-information measuring device, a preliminary diagnosis about whether the patient needs a proper diagnosis to be made by a doctor; and a physical-information transmitting means for transmitting, when the preliminary-diagnosis means makes a preliminary diagnosis that the patient needs a proper diagnosis to be made by a doctor, the measured physical information value to said at least one doctor-side device that has been selected by the patient.

2. A system according to claim 1, wherein the preliminary-diagnosis means comprises means for judging whether the measured physical information value falls within a first reference range, and means for making, when it is judged that the measured physical information value does not fall within the first reference range, a preliminary diagnosis that the patient needs a proper diagnosis to be made by a doctor, and wherein each of the doctor-side devices comprises a reference-range changing means for transmitting, to the preliminary-diagnosis means, a second reference range and changing the first reference range to the second reference range, so that the preliminary-diagnosis means judges whether the measured physical information value falls within the second reference range.

3. A system according to claim 1, wherein the preliminary-diagnosis means further comprises:

means for judging whether the measured physical information value falls within a first reference range proper for the patient;

means for making, when it is judged that the measured physical information value does not fall within the first reference range, a preliminary diagnosis that the patient needs a proper diagnosis to be made by a doctor; and a memory device which stores a plurality of first reference ranges respectively proper for a plurality of patients.

4. A system according to claim 3, wherein each of the doctor-side devices comprises a reference-range changing means for transmitting, to the preliminary-diagnosis means, a second reference range proper for the patient and changing the first reference range proper for the patient to the second reference range proper for the patient, so that the preliminary-diagnosis means judges whether the measured physical information value falls within the second reference range proper for the patient.

5. A system according to claim 1, wherein the patient-side device further comprises:

a display device; and a display control means for controlling the display device to display the preliminary diagnosis made by the preliminary-diagnosis means.

6. A system according to claim 5, wherein the preliminary-diagnosis means comprises a preliminary-diagnosis transmitting means for transmitting the preliminary diagnosis to the patient-side device.

7. A system according to claim 1, comprising a plurality of patient- side devices for a plurality of patients, respectively, each of the plurality of patient-side devices including at least one physical-information measuring device which measures at least one current physical information value from one of the plurality of patients corresponding to each patient-side device, wherein the preliminary-diagnosis means comprises a memory device which stores, for each of the plurality of patients, at least one past physical information value which had been measured by the physical-information measuring device of one of the plurality of patient-side devices corresponding to each patient, and wherein the physical-information transmitting means transmits, to the selected doctor-side device, the measured current physical information value with the measured past physical information value stored for each patient in the memory device.

8. A system according to claim 1, wherein said at least one physical-information measuring device comprises at least one device selected from the group consisting of a blood-pressure measuring device, a pulse-wave-propagation-velocity-relating-information measuring device, a body-weight meter, a pedometer, and a clinical thermometer.

9. A system according to claim 1, further comprising a communication network which connects the patient-side device to each of the doctor-side devices, so that said each of the doctor-side devices can receive the measured physical information value of the patient from the patient-side device.

10. A system according to claim 9, further comprising a central control device which is connected via the communication network to the patient-side device and the doctor-side devices, wherein the central control device comprises at least one of the preliminary-diagnosis mean and the physical-information transmitting means.

11. A system according to claim 1, wherein the selected doctor-side device further comprises:

an input device which is operable by a doctor to input a proper diagnosis made by the doctor based on the measured physical information value transmitted to said selected doctor-side device; and a proper-diagnosis transmitting means for transmitting the proper diagnosis to the patient-side device.

12. A system according to claim 11, wherein the patient-side device further comprises a display device which displays the proper diagnosis transmitted from the selected doctor-side device.

13. A remote diagnosis system comprising:

at least one patient-side device including at least one physical-information measuring device which measures at least one current physical information value from at least one patient;

a plurality of doctor-side devices which are provided in a plurality of medical institutions, respectively, that are remote from the patient-side device and each of which can receive the measured physical information value of the patient from the patient-side device;

a preliminary-diagnosis means for making, based on the physical information value measured by the physical-information measuring device, a preliminary diagnosis about whether the patient needs a proper diagnosis to be made by a doctor; and a physical-information transmitting means for transmitting, when the preliminary-diagnosis means makes a preliminary diagnosis that the patient needs a proper diagnosis to be made by a doctor, the measured physical information value to each of the plurality of doctor-side devices.

14. A system according to claim 13 wherein the preliminary-diagnosis means comprises means for judging whether the measured physical information value falls within a first reference range, and means for making, when it is judged that the measured physical information value does not fall within the first reference range, a preliminary diagnosis that the patient needs a proper diagnosis to be made by a doctor, and wherein each of the doctor-side devices comprises a reference-range changing means for transmitting, to the preliminary-diagnosis means, a second reference range and changing the first reference range to the second reference range, so that the preliminary-diagnosis means judges whether the measured physical information value falls within the second reference range.

15. A system according to claim 13, wherein the preliminary-diagnosis means further comprises:

means for judging whether the measured physical information value falls within a first reference range proper for the patient;

means for making, when it is judged that the measured physical information value does not fall within the first reference range, a preliminary diagnosis that the patient needs a proper diagnosis to be made by a doctor; and a memory device which stores a plurality of first reference ranges respectively proper for a plurality of patients.

16. A system according to claim 15, wherein each of the doctor-side devices comprises a reference-range changing means for transmitting, to the preliminary-diagnosis means, a second reference range proper for the patient and changing the first reference range proper for the patient to the second reference range proper for the patient, so that the preliminary-diagnosis means judges whether the measured physical information value falls within the second reference range proper for the patient.

17. A system according to claim 13, wherein the patient-side device further comprises:

a display device; and a display control means for controlling the display device to display the preliminary diagnosis made by the preliminary-diagnosis means.

18. A system according to claim 13, comprising a plurality of patient-side devices for a plurality of patients, respectively, each of the plurality of patient-side devices including at least one physical-information measuring device which measures at least one current physical information value from one of the plurality of patients corresponding to each patient-side device, wherein the preliminary-diagnosis means comprises a memory device which stores, for each of the plurality of patients, at least one past physical information value which had been measured by the physical-information measuring device of one of the plurality of patient-side devices corresponding to each patient, and wherein the physical-information transmitting means transmits, to said each doctor-side device, the measured current physical information value with the measured past physical information value stored for each patient in the memory device.

19. A system according to claim 7, wherein said plurality of doctor-side devices comprise at least three doctor-side devices, and wherein the patient-side device further comprises a doctor-side-device selecting device operable by the patient to select at least two doctor-side devices from said at least three doctor-side devices, and the physical-information transmitting means transmits, when the preliminary-diagnosis means makes the preliminary diagnosis that the patient needs the proper diagnosis, the measured physical information value to each of said at least two selected doctor-side devices.

20. A system according to claim 13, wherein said at least one physical-information measuring device comprises at least one device selected from the group consisting of a blood-pressure measuring device, a pulse-wave-propagation-velocity-relating-information measuring device, a body-weight meter, a pedometer, and a clinical thermometer.

* * * * *